US012797682B2

(12) United States Patent
Flaction et al.

(10) Patent No.: US 12,797,682 B2
(45) Date of Patent: Nov. 17, 2026

(54) INTEGRATED PORTABLE DEVICE AND METHOD IMPLEMENTING AN ACCELEROMETER FOR ANALYZING BIOMECHANICAL PARAMETERS OF A STRIDE

(71) Applicant: Slyde Analytics LLC, Houston, TX (US)

(72) Inventors: Patrick Flaction, Chandolin-près-Savièse (CH); Jacques Quièvre, Rozay en Brie (FR); Jean-Benoît Morin, Genilac (FR)

(73) Assignee: Slyde Analytics LLC, Houston, TX (US)

( * ) Notice: Subject to any disclaimer, the term of this patent is extended or adjusted under 35 U.S.C. 154(b) by 320 days.

(21) Appl. No.: 18/527,051

(22) Filed: Dec. 1, 2023

(65) Prior Publication Data

US 2024/0091589 A1 Mar. 21, 2024

Related U.S. Application Data

(63) Continuation of application No. 15/850,932, filed on Dec. 21, 2017, now Pat. No. 11,833,391, which is a (Continued)

(51) Int. Cl.
*A63B 24/00* (2006.01)
*A61B 5/00* (2006.01)
(Continued)

(52) U.S. Cl.
CPC ........ *A63B 24/0006* (2013.01); *A61B 5/1038* (2013.01); *A61B 5/112* (2013.01);
(Continued)

(58) Field of Classification Search
CPC .............. A63B 24/0006; A61B 5/1038; A61B 5/112; A61B 5/1122; A61B 5/6831;
(Continued)

(56) References Cited

U.S. PATENT DOCUMENTS

| | | | |
|---|---|---|---|
| 5,056,783 | A | 10/1991 | Matcovich et al. |
| 5,125,412 | A | 6/1992 | Thornton |

(Continued)

FOREIGN PATENT DOCUMENTS

| | | | |
|---|---|---|---|
| DE | 4426302 | A1 | 2/1996 |
| EP | 0125404 | A1 | 11/1984 |

(Continued)

OTHER PUBLICATIONS

Lee JB, Sutter KJ, Askew CD, Burkett BJ. Identifying symmetry in running gait using a single inertial sensor. Journal of Science and Medicine in Sport. Sep. 1, 2010;13(5):559-563 (Year: 2010).*

(Continued)

*Primary Examiner* — Peter D Nolan
(74) *Attorney, Agent, or Firm* — Volpe Koenig

(57) ABSTRACT

Method implementing an accelerometer (17) for analyzing biomechanical parameters of the stride of a runner, comprising:

(a) fastening a device (1) on the torso of the runner, said device being electrically self-sufficient and comprising a triaxial accelerometer (17), a chronograph (16), a digital processor (19) and a display (11);

(b) measuring a sequence of acceleration data in at least the vertical direction ($a_v$) using said accelerometer, while the runner runs a certain distance (D) along a running course;

(c) during or at the end of said running course, having said processor calculate the biomechanical parameters of the stride, including the lowering (A) of the center of (Continued)

gravity and/or the elevation (E) of the center of gravity and/or the sum of the lowering and of the elevation of the center of gravity and/or the vertical mechanical work of the center of gravity (CG) of said runner, on the basis of said acceleration data, of said distance (D) and of a period of time (T) measured by said chronograph (16); and (d) displaying said parameters on said display (11).

20 Claims, 6 Drawing Sheets

Related U.S. Application Data continuation of application No. 15/090,254, filed on Apr. 4, 2016, now Pat. No. 9,873,018, which is a continuation of application No. 13/715,236, filed on Dec. 14, 2012, now Pat. No. 9,320,457, which is a continuation of application No. PCT/EP2011/059503, filed on Jun. 8, 2011.

(51) Int. Cl.

| | |
|---|---|
| ***A61B 5/103*** | (2006.01) |
| ***A61B 5/11*** | (2006.01) |
| ***G01C 22/00*** | (2006.01) |
| ***G01P 15/18*** | (2013.01) |
| ***G06V 40/20*** | (2022.01) |

(52) U.S. Cl.

CPC .......... *A61B 5/1122* (2013.01); *A61B 5/6831* (2013.01); *G01C 22/006* (2013.01); *G01P 15/18* (2013.01); *G06V 40/23* (2022.01)

(58) Field of Classification Search

CPC .......... A61B 2562/0219; G01C 22/006; G01P 15/18; G06V 40/23; G06F 2218/00

See application file for complete search history.

(56) References Cited

U.S. PATENT DOCUMENTS

| | | | | |
|---|---|---|---|---|
| 5,263,491 | A | 11/1993 | Thornton | |
| 5,474,083 | A | 12/1995 | Church et al. | |
| 5,788,655 | A | 8/1998 | Yoshimura et al. | |
| 5,976,083 | A | 11/1999 | Richardson et al. | |
| 6,148,280 | A | 11/2000 | Kramer | |
| 6,183,425 | B1 | 2/2001 | Whalen et al. | |
| 6,397,151 | B1 | 5/2002 | Yamagishi et al. | |
| 6,997,882 | B1 | 2/2006 | Parker et al. | |
| 7,827,000 | B2 * | 11/2010 | Stirling | A61B 5/6807 73/865.4 |
| 7,857,772 | B2 | 12/2010 | Bouvier et al. | |
| 8,055,469 | B2 * | 11/2011 | Kulach | A63B 24/0062 73/865.4 |
| 8,060,337 | B2 * | 11/2011 | Kulach | A61B 5/1112 73/865.4 |
| 8,157,707 | B2 | 4/2012 | Flaction | |
| 2003/0018430 | A1 | 1/2003 | Ladetto et al. | |
| 2004/0143452 | A1 * | 7/2004 | Pattillo | A61B 5/1038 600/595 |
| 2004/0167641 | A1 | 8/2004 | Kawai et al. | |
| 2006/0293613 | A1 | 12/2006 | Fatehi et al. | |
| 2007/0027369 | A1 | 2/2007 | Pagnacco et al. | |
| 2007/0062279 | A1 | 3/2007 | Chan et al. | |
| 2008/0190202 | A1 * | 8/2008 | Kulach | A63B 24/0062 73/514.01 |
| 2008/0214360 | A1 * | 9/2008 | Stirling | A61B 5/6807 482/9 |
| 2008/0288200 | A1 | 11/2008 | Noble | |
| 2009/0018794 | A1 | 1/2009 | Meriheina | |
| 2009/0069722 | A1 | 3/2009 | Flaction et al. | |
| 2010/0056957 | A1 | 3/2010 | Vuillerme et al. | |
| 2010/0117837 | A1 | 5/2010 | Stirling et al. | |
| 2010/0204616 | A1 | 8/2010 | Shears et al. | |
| 2010/0211349 | A1 | 8/2010 | Flaction et al. | |
| 2010/0250179 | A1 | 9/2010 | Mariano | |
| 2011/0022349 | A1 * | 1/2011 | Stirling | A61B 5/1038 702/141 |
| 2011/0152727 | A1 | 6/2011 | Ten Kate | |
| 2011/0231101 | A1 | 9/2011 | Bidargaddi et al. | |
| 2012/0035509 | A1 * | 2/2012 | Wilson | A61B 5/1038 600/592 |
| 2013/0041291 | A1 * | 2/2013 | Soubeyrat | A61B 5/1038 600/595 |
| 2013/0053990 | A1 * | 2/2013 | Ackland | G06Q 30/02 700/91 |

FOREIGN PATENT DOCUMENTS

| | | | |
|---|---|---|---|
| EP | 0418548 | A1 | 3/1991 |
| EP | 1253404 | A2 | 10/2002 |
| EP | 1466557 | A2 | 10/2004 |
| EP | 1754521 | A1 | 2/2007 |
| EP | 1764583 | A2 | 3/2007 |
| EP | 1862765 | A1 | 12/2007 |
| EP | 1897598 | A1 | 3/2008 |
| EP | 1992389 | A1 | 11/2008 |
| EP | 2027817 | A1 | 2/2009 |
| GB | 2415788 | A | 1/2006 |
| JP | 2-203842 | A | 8/1990 |
| JP | 11-137539 | A | 5/1999 |
| JP | 2001-1519185 | A | 10/2001 |
| JP | 2005-224318 | A | 8/2005 |
| JP | 2006-102156 | A | 4/2006 |
| JP | 2006175206 | A | 7/2006 |
| JP | 2006271893 | A | 10/2006 |
| JP | 2009101108 | A | 5/2009 |
| JP | 2009106387 | A | 5/2009 |
| JP | 2009539455 | A | 11/2009 |
| WO | WO 99/18480 | | 4/1999 |
| WO | WO-0156470 | A1 | 8/2001 |
| WO | WO-03032826 | A2 | 4/2003 |
| WO | WO-2005074795 | A1 | 8/2005 |
| WO | WO-2005091113 | A2 | 9/2005 |
| WO | WO-2006030065 | A1 | 3/2006 |
| WO | WO-2006/038712 | A1 | 4/2006 |
| WO | WO-2007017471 | A1 | 2/2007 |
| WO | WO-2007036611 | A1 | 4/2007 |
| WO | WO-2007/102134 | A2 | 9/2007 |
| WO | WO-2007107491 | A1 | 9/2007 |
| WO | WO-2009/018794 | A2 | 2/2009 |
| WO | WO-2009024600 | A1 | 2/2009 |
| WO | WO-2009094746 | A1 | 8/2009 |
| WO | WO-2009/108887 | A2 | 9/2009 |
| WO | WO-2010046448 | A1 | 4/2010 |
| WO | WO-2010073044 | A1 | 7/2010 |
| WO | WO-2010150260 | A1 | 12/2010 |

OTHER PUBLICATIONS

Rigoberto MM, Toshiyo T, Masaki S. Smart phone as a tool for measuring anticipatory postural adjustments in healthy subjects, a step toward more personalized healthcare. In 2010 Annual International Conference of the IEEE Engineering in Medicine and Biology Aug. 31, 2010 (pp. 82-85) (Year: 2010).*

C. Van Dongen, "Suivez Vso Penchants . . . Pour Un Suivi des Lombalgiques Par le Detecteur de Posture Programmable," Mains Libres, No. 8, pp. 313-324, 2006, www.mainslibres.ch.

G. A. Cavagna et al., "External Work in Walking," Journal of Applied Physiology, Jan. 1963, vol. 18, pp. 1-9.

G. A. Cavagna et al., "Mechanical Work in Running," Journal of Applied Physiology, Mar. 1964, vol. 19, pp. 249-256.

European Search Report for EP16157843, dated Jun. 9, 2016, 11 pages.

(56) References Cited

OTHER PUBLICATIONS

European Search Report for EP16157853, dated Jun. 10, 2016, 11 pages.

* cited by examiner

INTEGRATED PORTABLE DEVICE AND METHOD IMPLEMENTING AN ACCELEROMETER FOR ANALYZING BIOMECHANICAL PARAMETERS OF A STRIDE

RELATED APPLICATIONS

The present application is a continuation of U.S. application Ser. No. 15/850,932 filed Dec. 21, 2017, now U.S. Pat. No. 11,833,391, which is a continuation of the US application number Ser. No. 15/090,254 filed Apr. 4, 2016 (publication number US20160213975), now U.S. Pat. No. 9,873,018, which is a continuation of the U.S. application Ser. No. 13/715,236 filed Dec. 14, 2012 (publication number US20130190657), now U.S. Pat. No. 9,320,457 issued Apr. 26, 2016, which is a continuation of the international application PCT/EP2011/059503, filed on Jun. 8, 2011, which claims priority from Swiss patent application CH2010/973, filed on Jun. 16, 2010, the contents of all of which are hereby incorporated by reference.

TECHNICAL FIELD

The present invention relates to a method and an integrated portable device provided with an accelerometer for measuring biomechanical parameters of a stride in running.

STATE OF THE ART

The results of a runner depend essentially on cardiovascular endurance qualities and on the mechanical efficiency of the stride. Many devices and tests are known in the state of the art for measuring progress in terms of cardiovascular performance. For example, many runners train with a heart rate monitor that shows them their heart rate at any time, whilst different tests enable for example the maximum oxygen volume taken from the lungs and used by the muscles per time unit ($V0_2$ max) to be measured.

The present invention relates more precisely to methods and devices for measuring the biomechanical efficiency of the stride. By improving the efficiency of each stride, the runner is able to run faster or longer with a given quantity of energy. It is however difficult, even for a runner accompanied by an experienced coach, to objectively measure the efficiency of his/her stride and improve it without resorting to measuring devices. In particular, there is a need for a method and device that are simple, portable, self-sufficient and capable of supplying, in real time and immediately after the run, parameters that are useful for analyzing the stride.

It is also difficult for a runner to avoid the risk of overtraining, of fatigue and even of injury. The warning signs are difficult to perceive and there is in the prior art no simple device for detecting and assessing the risk of muscle fatigue or of injury.

Treadmills are frequently used in the state of the art that are provided for example with force sensors enabling the reaction force on the floor each time the foot rests on it to be measured with a very high accuracy. These devices are however costly and reserved for professional use by coaches, in sports halls or in hospitals for example. They allow only the force to be measured when the foot touches the floor but do not supply any indication as to the runner's motion when the feet are in the air. Furthermore, the running style on a treadmill differs considerably from that which is adopted outdoors or during a long-lasting run, so that the indications supplied by these devices need to be interpreted.

Wristwatches are also known that are provided with an inertial sensor and designed first and foremost for occasional runners. One example is described in EP1862765. The wrists of a runner, however, follow a very different trajectory from that of the athlete's center of mass and even briefly return backwards at each step. Such devices are possibly useful for approximately evaluating the distance travelled or the number of calories expended during a running session, but are however incapable of analyzing the stride accurately.

In this context, the expressions "center of mass" and "center of gravity" must be considered equivalent. They refer to the barycenter of a runner. If, because of the runner's position, the center of mass or center of gravity is located outside the runner's body, the center of mass or center of gravity coincides with the point closest to the center of mass or center of gravity and belongs to the runner's body. In other words, the center of mass is located practically at the place where the device and/or sensor is fastened, on the torso, generally close to the waist.

U.S. Pat. No. 6,397,151 describes a wristwatch designed for combat sports and provided with an accelerometer capable of measuring a sequence of accelerations of the forearm during a hit. DE4426302 describes another system designed to measure accelerations during combat sports. These devices are not suited for running.

Different companies also suggest placing an accelerometer in or on the shoe. One example is described in WO09094746. This location enables the trajectory of one of the two feet to be followed very closely. It is however far removed from the runner's center of gravity and therefore does not make it possible to detect for example whether the runner's torso oscillates or sways unsuitably. Furthermore, this sensor ignores what the other foot is doing and does not allow for example the runner's flight time duration at each stride to be measured. It also does not allow the behavior of the center of gravity to be analyzed and does not therefore allow an accurate analysis of the stride.

EP1897598 describes a training aid device for different sports. It uses an accelerometer on the ankle or knees. Again, these different locations are removed from the athlete's center of gravity and from his plane of symmetry, so that the measurements supplied are inaccurate or not relevant for analyzing the running style.

WO2009/094746 describes an accelerometer capable of determining itself its location on the foot, on the wrist etc.

U.S. Pat. No. 6,148,280 describes a system comprising accelerometers and gyroscopes distributed on the athlete's entire body in order to analyze the body's trajectory during a movement. The data supplied by the different sensors are transmitted to a remote personal computer. This system therefore does not make it possible to supply in real time, immediately after a run, useful parameters for analyzing the stride. This system is particularly complex, costly and fragile. A comparable device is also described in EP418548.

Devices are also known that are provided with an inertial sensor enabling muscular parameters of an athlete to be measured by means of short tests. U.S. Pat. No. 5,474,083 for example describes a device designed to measure the muscular activity of an athlete during short weight-lifting exercises. This device is only suitable for short tests and not for running for example. Other examples are also described in patent applications WO07107491, EP2027817 or WO2010046448 filed by the applicant. These devices are designed first and foremost for muscle training and make it possible for example to measure the force, the power or the stiffness of muscles by means of series of jumps for example. Although these muscular parameters are useful also for runners, it is not suggested for them to be used for analyzing the stride nor for them to be determined from running tests.

WO2007036611, which further enables the maximum weight a person is capable of lifting to be determined, suffers from the same limitations.

US20090018794 describes a device for measuring the progress of a moving person by means of an inertial sensor placed close to the center of gravity. The speed and the other parameters are determined on the basis of the maximum vertical acceleration or possibly of the minimum vertical acceleration by using a proportionality factor k. This factor k, which is not described in the document, depends however necessarily on the type of displacement, on the means of locomotion and on the running style; the computed results are thus equivocal or depend on unverifiable hypotheses about the factor k. The aim of this document is first and foremost to add indications obtained at each stride in order to display for example the travelled distance, the number of steps or the speed, but not to display parameters enabling the efficiency of each stride to be analyzed.

EP1754521 describes a method enabling the efficiency of a runner's stride to be determined by measuring instantaneous accelerations of the runner. The speeds can be determined only to within one constant. This device calculates and displays a global efficiency index which is the ratio of the sum of the harmonic accelerations over the speeds. However, the user does not know what s/he must do in order to improve this global efficiency index and the device does not supply other parameters related to his/her stride and enabling the runner to improve directly his/her running style.

WO2007017471 describes a method and a device for determining a runner's speed by means of an accelerometer by counting the number and frequency of direction changes in the vertical acceleration.

The devices comprise an inertial sensor as an aid for running determining in general the travelled distance through a double integration of the acceleration in the horizontal direction. This measurement is however inaccurate for various reasons. First, the fact itself of integrating produces an accumulation of errors and inaccuracies from the sensor. Running will generate considerable shocks at each stride, so that the acceleration signal is very noisy, in particular if the accelerometer is carried on the members, for example in the shoe, on the ankle or wrist. Furthermore, it is difficult to determine the anteroposterior direction in which the runner progresses and to eliminate the components due to the vertical or transversal acceleration caused by the body's swaying. This yields an imprecise determination of the travelled distance and a calculation of all the parameters based on this distance that also suffers from this imprecision.

Furthermore, U.S. Pat. No. 5,788,655 is also known which describes a device provided with an accelerometer and with a liquid crystal display in order to measure the user's level of activity and the number of calories burned in a day. This device is not designed for sports training and does not enable the muscular or biomechanical parameters of an athlete to be measured.

WO2005/074795 describes a device also designed to being connected to the body of a person to determine the level of activity over a long period, for example a day or a week. A comparable device is also described in WO03032826.

EP1992389 describes a sensor provided with an accelerometer, with a gyroscope, with a GPS receiver, with a magnetometer and with a cardiometer in order to monitor the efforts of an athlete. The device is complex and does not supply useful indications for improving the stride during a run.

Moreover, other devices are known that are based on accelerometers and gyroscopes and that enable the trajectory of a sports accessory, for example a baseball bat (U.S. Pat. No. 5,056,783) or a golf club, to be analyzed.

US20080288200 relates to a device for measuring the posture and intensity of a physical activity comprising a triaxial accelerometer. This device makes it possible to calculate parameters, notably the PEE (Potential Energy Expenditure) and the KEE (Kinetic Energy Expenditure) that do not depend on the distance travelled by the runner nor on the time measured by a chronograph.

EP1253404 describes a device that determines the evolution of the position of a pedestrian from the context and enables the total distance travelled by the user, his/her speed as well as the distance between two impacts on the ground to be calculated.

U.S. Pat. No. 5,976,083 concerns a device for monitoring, estimating and predicting a user's level of fitness. The device comprises a fastening system around the user's chest, at the level of his/her heart. The device uses personal data of the user, the vertical accelerations given by an accelerometer and the real-time clock to calculate the distance travelled by the user. The parameters computed during the fitness estimation/prediction by the device comprise the duration of the session, the total of the calories burned, the distance travelled, the fitness, the average heart rate, the EE (energy expenditure) slope and intercept relative to the heart rate. These results are supplied upon request from the user.

WO2006030065 describes a device for detecting the movement of a human being by a movement sensor carried on the torso, on the shoes or on the wrist of a human being. A measurement signal is compared to a predetermined reference signal that can be measured in a similar manner on a known human being. A recognition operation is performed on the basis of the comparison between the measurement signal and the predetermined reference signal, with the recognition operation resulting in the recognition or non-recognition. This device is not suited for analyzing biomechanical parameters of a runner's stride, the aim being the recognition of the movement of a human being, for identifications and/or verifications.

EP1764583 relates to a device for measuring information of a runner such as the total running time, the average and maximum speed, the total distance travelled and the average and maximum heart rate. The device, which includes an accelerometer measuring only the vertical acceleration, is fastened on the runner's torso and communicates with another receiver-device carried on the runner's wrist, on which the information is displayed.

WO2005091113 describes a device and method for evaluating the movement of a pedestrian, consisting in determining at least one position of at least one identified part of the pedestrian, to project the position or positions onto at least one plane and to calculate the movement from the position or positions projected onto this plane. The device, without chronograph, only makes it possible, and this in a complicated manner, to determine the orientation of the members and the orientation and length of a step.

All these documents do not make it possible to determine in a simple and immediate manner the biomechanical parameters of a runner's stride linked to his/her center of gravity, notably linked to the displacement of his/her center of gravity. The expression "vertical displacement of the center of mass or center of gravity" refers to its ideal displacement, which occurs in a horizontal plane. In other words, this expression designates the undulation of the center of mass or center of gravity relative to the horizontal plane to which the center of mass or center of gravity belonged at the beginning of the run, this undulation resulting from the sum of the lowering and elevation of the center of mass or center of gravity relative to this horizontal plane.

This parameter is very important for a runner who runs short distances, for example 200 m, in a short lapse of time: in order to run in the most efficient way possible, his/her center of gravity should ideally not move vertically. This parameter is also important for a marathon runner, who on the contrary uses the vertical oscillation of the center of mass and thus the elastic rebound of his/her legs on the ground.

There is thus a need for a device and method that make it possible to determine in a simple and immediate manner biomechanical parameters of a runner's stride linked to his/her center of gravity, notably linked to the vertical displacement of his/her center of gravity.

BRIEF SUMMARY OF THE INVENTION

One aim of the present invention is to propose a method and a device free from the limitations of the known methods and devices, in particular a method and a device that make it possible to determine in a simple and immediate manner biomechanical parameters of a runner's stride linked to his/her center of gravity, notably linked to the vertical displacement of his/her center of gravity.

Another aim of the invention is to propose a device and method that are more accurate, more cost-effective, more compact, easier to handle and/or that supply results practically instantaneously and in real-time.

Another aim of the invention is to propose a device and a method for measuring and analyzing the kinematics of the movement (acceleration, speed and position of the center of mass of a runner) as well as, much more broadly, all of the parameters that characterize the technical qualities and physical capacities of the runner.

Another aim of the invention is to propose a device and method that are self-sufficient and portable, and capable of determining parameters that are useful for analyzing for the runner to improve the regularity and efficiency of his/her stride and reduce the risk of fatigue or injury.

The invention is based notably on the observation that a full range of biomechanical parameters, among them the lowering and elevation of the center of mass, can unexpectedly be measured and calculated with significant accuracy by means of a simple, judiciously placed accelerometer. Some of these parameters had never been measureable previously whilst others could be measured only with much more complex and non-self-sufficient devices, for example by requiring a separate analysis on a portable computer to extract certain parameters.

According to the invention, these aims are achieved notably by means of an integrated portable device and a method implementing an accelerometer for analyzing biomechanical parameters of the stride of a runner, comprising:

(a) fastening a device on the torso of the runner, said device being electrically self-sufficient and comprising a triaxial accelerometer, a chronograph, a digital processor and a display;

(b) measuring a sequence of acceleration data in at least the vertical direction using said accelerometer, while the runner runs a certain distance along a running course;

(c) during or at the end of said running course, having said processor calculate the biomechanical parameters of the stride, including the lowering (A) of the center of gravity and/or the elevation (E) of the center of gravity and/or the sum of the lowering and of the elevation of the center of gravity and/or the vertical mechanical work of the center of gravity (CG) of said runner, on the basis of said acceleration data, of said distance and of a period of time measured by said chronograph; and (d) displaying said parameters on said display.

This method affords notably the advantage of enabling reliable parameters to be measured and computed, even with a simplified device. The reliability is notably achieved by fastening the accelerometer close to the runner's center of gravity, by means of a belt or clip. The duration. The chronograph integrated into the device determines the duration of the run. The measurement of the total distance travelled also does not depend on the accelerometer's accuracy, either because it is implicit and predetermined, or because the user choses/enters it, or also through satellite receiver of GPS type for example.

The invention is also based on the surprising observation that several parameters useful for running training can be determined on the basis of acceleration measurements performed with the inventive device. The invention also relates to different means and method steps enabling a whole series of parameters to be calculated in a manner different from the prior art, by using exclusively acceleration measurements, and with remarkable accuracy. The invention thus provides a device capable of calculating and displaying a whole series of biomechanical parameters directly usable by the runner or his/her coach.

The invention thus provides a new device and a new method for calculating biomechanical parameters of the stride which were either calculated differently in the prior art, with more complex means (triaxial gyroscopes, portable computer etc.), or even parameters that were impossible to calculate or which no one had ever made the effort of measuring.

The position of the device in the lower back or on the belly enables any asymmetry between the movements performed by each of the two legs at each stride to be measured. It is thus possible to measure the asymmetry of the muscular and biomechanical parameters of both legs with a single sensor judiciously placed and with an adequate processing of the signals.

The biomechanical parameters calculated include for example the distance travelled by the runner's center of mass for the duration when the foot is in contact with the ground (distance during contact). The beginning and the end of the duration is determined on the basis of the measurement of the acceleration, for example of the acceleration in the vertical or anteroposterior direction, which changes suddenly when the foot leaves or reaches the ground. The measurement of this distance is obtained by multiplying the speed in the anteroposterior direction by the contact time. Since the accelerometer is placed close to the runner's center of mass, it is also possible to determine accurately the vertical lift-off speed as well as the takeoff angle of the center of gravity.

The calculated biomechanical parameters can also include for example the angle with which the leg lands on the ground as well as the angle of the leg support area, which is the angle formed by the leg between the moment when the foot touches the ground and the moment when the foot leaves the ground. In the prior art, these different angles were determined on the basis of high-frequency video images and thus required complex equipment incapable of supplying a result in real-time. It has been discovered in the frame of the invention that signal processing operations and computation operations on the basis sequences of acceleration data supply a simpler, more economical and more reliable means of measuring these angles in a near-instantaneous manner.

The method and device also enable a stride regularity index to be determined in a new manner and with new means. The regularity index depends for example on the dispersion of the different parameters measured at each stride, for example on the dispersion of the reactivity or the dispersion of another parameter relating to the stride.

Generally, the method also enables a stride efficiency index to be determined in a new manner and with new means, on the basis of the distance of the leg when in contact with the ground, of the contact time on the ground and of the stiffness of the runner's leg, and of the stride length.

Generally, the method enables at least one indicator of muscular fatigue to be indicated, i.e. an indicator whose absolute value or temporal evolution can be used for example to reveal abnormal fatigue. Use of an accelerometer to determine the level of fatigue affords very simple possibilities for an athlete to optimize his/her training whilst avoiding the risk of performance plateauing in case of overtraining.

Calculated biomechanical parameters can also include for example an asymmetry between at least one parameter of the left leg and at least one corresponding parameter of the right leg. For example, the device can detect and display a parameter making it possible to deduce that the length of the strides made with one leg touching the ground is longer than with the other, or that there are different touchdown or takeoff angles. These differences can for example correspond to differences in the length of the leg or in muscle training (notably when these differences persist during long periods or during several successive training sessions); they can also constitute warning or predictor signs of injury or fatigue. The invention thus also relates to a new use of an accelerometer as device for detecting the risk of injury when running.

Furthermore, the method also allows at least one indicator of risk of injury to be indicated, i.e. an indicator whose absolute value or temporal evolution shows a risk of injury. For example, a quick variation or variation at unusual levels of the stiffness of the leg muscles will often herald an injury; this variation can be detected and displayed to protect the runner.

The calculated biomechanical parameters can also include for example the vertical speed of the center of mass during one stride and/or the vertical displacement of the center of mass during one stride and/or the takeoff angle of the center of mass. An efficient running style will generally imply a displacement of the runner's center of mass in a direction that is as horizontal as possible, with a vertical speed as constant and as close to zero as possible, and a horizontal speed in the anteroposterior axis as constant and elevated as possible. A sequence of acceleration data in at least the anteroposterior is preferably also measured by said accelerometer and processed separately from the sequence of acceleration data in the vertical direction in order to calculate at least some of the parameters.

The calculated biomechanical parameters can also include for example the rhythm of the steps, the contact time with the ground, the flight time, the average acceleration when in contact with the ground, the maximum force when resting on the ground, the horizontal speed of the center of mass during ground contact, the stiffness or reactivity of the muscles, for example the muscles of one leg or of both legs in a differentiated manner.

In one embodiment, a sequence of the acceleration data in at least the lateral direction is also measured and processed separately of the sequence of acceleration data in the vertical direction in order to calculate at least some of the parameters, for example the rotation and swaying of the torso at each stride. This sensor can also be used for distinguishing between the strides made with the left foot and those made with the right foot.

The vertical direction is determined for example by measuring gravity when the runner at a standstill. The anteroposterior direction is determined or corrected advantageously during the run by determining the spatial direction in which the horizontal displacement is greater.

A transformation of the "device-runner" frame of reference is preferably performed since the axes of the accelerometer never coincide perfectly with the vertical respectively horizontal and lateral axes of the runner. Consequently, the triaxial data from the accelerometer are projected along the runner's vertical, horizontal and/or lateral axes respectively. The device thus supplies one, two or three sequences of acceleration data that do not necessarily correspond to the axes of the accelerometer and that are processed and used independently for computing the parameters.

The device advantageously proposes a personalized training plan depending on the parameters and designed to improve the technical or muscular qualities of the user, for example a runner. For example, the training plan can be optimized for training preferably the athlete's weak points. The exercises can comprises exercises different from running, including jumps, muscle or stretching exercises, etc. The device can also be used during these exercises for monitoring the execution of said training plan.

The device can also distinguish between the strides made on flat, uphill or downhill segments of the running course and displays parameters and/or recommendations that are differentiated for these three types of segments. Determining the slope can be performed by the accelerometer, with a satellite receiver, a pressure sensor or on the basis of indications supplied by the runner.

The system can provide advice, depending on the runner's typology, as to the ideal type of shoe for improving the efficiency of the displacement and the protection of the musculotendinous system.

According to one aspect, the invention also relates to a method implementing an accelerometer for analyzing biomechanical parameters of the stride of a runner, comprising:

(a) fastening a device on the torso of the runner, said device being electrically self-sufficient and comprising a triaxial accelerometer, a chronograph, a digital processor and a display;

(b) measuring a sequence of acceleration data in at least the vertical direction using said accelerometer, while the runner runs a certain distance along a running course;

(c) during or at the end of said running course, having said processor calculate the biomechanical parameters of the stride, including the lowering of the center of gravity and/or the elevation of the center of gravity and/or the sum of the lowering and of the elevation of the center of gravity and/or the vertical mechanical work of the center of gravity of said runner, on the basis of said acceleration data, of said distance and of a period of time measured by said chronograph; and (d) displaying said parameters on said display.

BRIEF DESCRIPTION OF THE FIGURES

Examples of embodiments of the invention are indicated in the description illustrated by the attached figures in which.

EXAMPLE(S) OF EMBODIMENTS OF THE INVENTION

Figure 1:
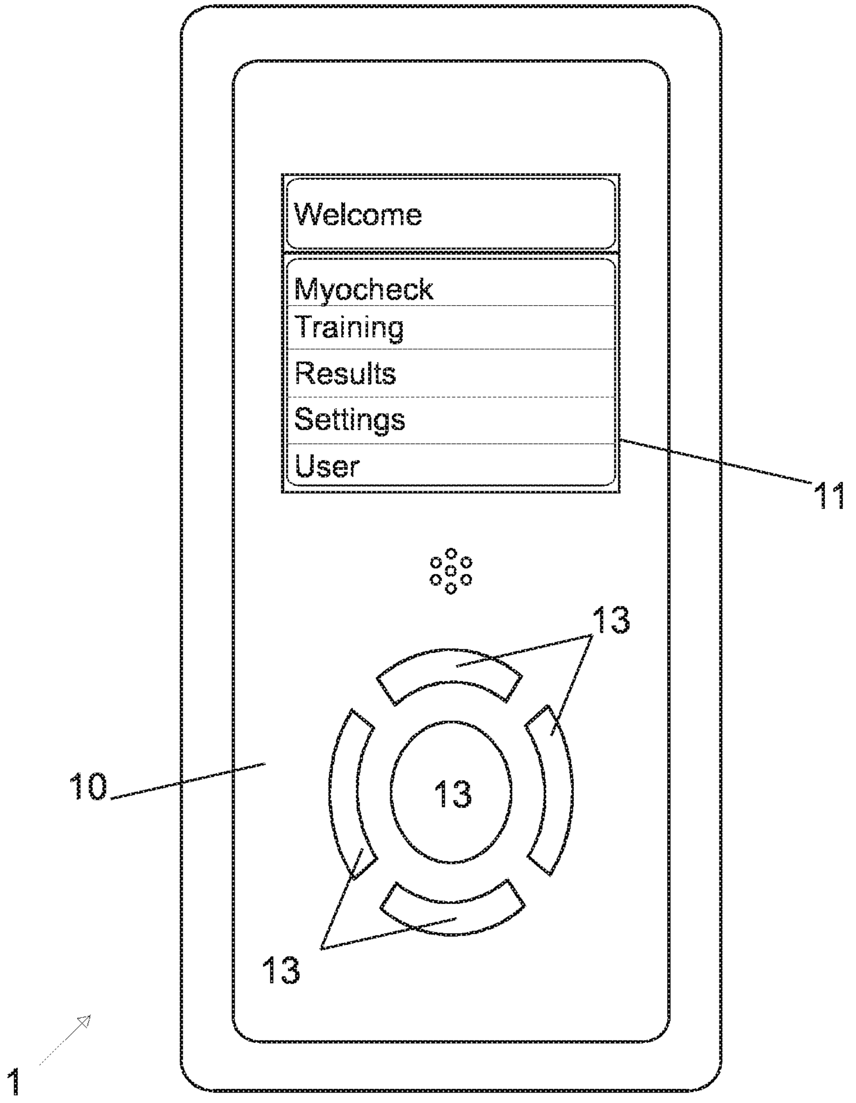
FIG. 1 illustrates an example of the device according to the invention.

An example of a device according to the invention is illustrated in FIG. 1. This device 1 includes a case, for example a plastic case with a weight of less than 100 grams, preferably less than 50 grams (including the contents). The athlete can attach this case to his/her hip, in the lower back or on the belly by means of a belt, for example an extensible belt closed by a hook-and-loop band, or a click fastened directly on the clothes. The belt allows a stable fastening close to the runner's center of gravity whilst minimizing the vibrations and displacements of the device relative to the center of mass.

The device further comprises a display 11, for example an alphanumeric or graphical display, preferably a liquid crystal display. This display makes it possible to display control menus, the memory status, the state of the battery 18 (FIG. 2), as well as numeric and qualitative parameters determined during and after the tests. Controls 13, for example buttons or other tactile elements, make it possible to navigate in the menus, to select options, to enter data and to select the results to be displayed. In the illustrated example, the device comprises four navigation buttons arranged around a central confirmation button.

The device preferably includes a triaxial accelerometer 17, for example an accelerometer based on a MEMS-type component, supplying distinct acceleration sequences along these three axes. The orientation of the device and/or of the accelerometer relative to the runner is measured at standstill and thus enables the device-runner" frame of reference to be calibrated and transformed in order to measure accelerations in a frame of reference linked to the runner. In one variant embodiment, triaxial data of the accelerometer are projected and memorized along a single one of the axes or along two axes or along three axes. The accelerometer can have a privileged axis that affords a higher accuracy, resolution, range of measurement and/or frequency of acquisition than the other axes. This privileged axis as advantageously oriented roughly vertically during a normal use, in order to improve the quality of the measurement in the vertical direction. The range of measurement along this privileged axis is preferably greater than ±8 G, or even greater than ±10 G. The resolution of this axis is preferably greater than 10 or even 12 bits.

In order to reduce its cost, its power consumption, its space requirements and its complexity, the device is advantageously not equipped with a gyroscope. Use of a gyroscope with one or several axes can however be conceived for certain applications or for calibrating and orienting the device in a more reliable manner.

Figure 2:
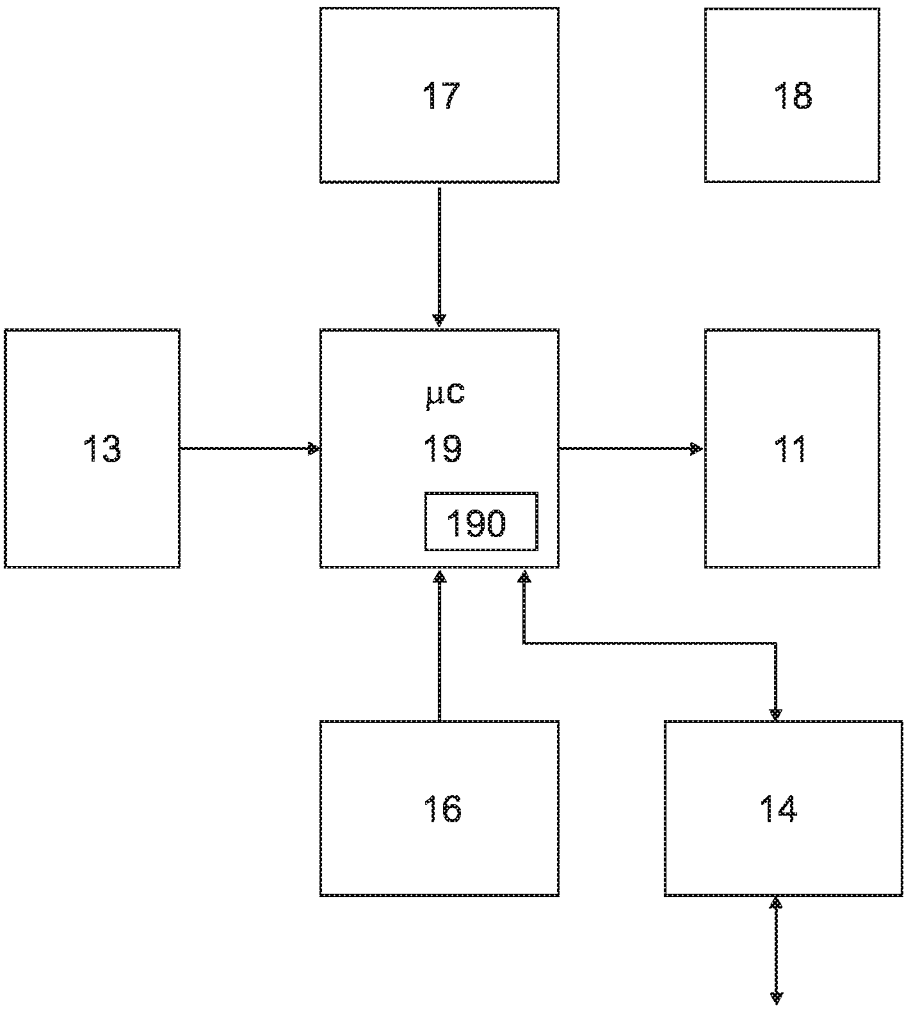
FIG. 2 is a simplified bloc diagram of the electronic components of the inventive device.

FIG. 2 is a simplified block diagram of the system's main components. The device 1 is preferably electrically self-sufficient and includes a battery 18, for example an accumulator charged through a USB connector or an appropriate charger. The battery supplies in particular a microprocessor 19 or a microcontroller provided with a RAM and/or EEPROM memory 190. The microprocessor executes an EEPROM-memory program that can be updated via a USB or Bluetooth interface for example, in order to control the display 11 and to analyze the acceleration data supplied by the accelerometer. This program thus allows the computation means to be controlled in order to determine the biomechanical parameters of the stride on the basis of the sequences of acceleration data measured along one or several axes.

The device also includes a chronograph for measuring temporal durations Δt, for example an electronic chronograph based on a real-time clock RTC 16, as well as a loud-speaker or a buzzer, not represented, controlled by the microprocessor 19 to generate alarms or sounds. An input-output Universal Asynchronous Receiver Transmitter (UART) module 14 enables data to be exchanged with external devices, for example to reprogram it and/or to transmit the measurement results to a personal computer, a mobile telephone or any other close-range data processing device. The UART module can be for example connected to a wired connector of the type USB or to a wireless interface of the type Bluetooth or Zigbee for example. It is also possible to provide a connector for a Flash memory card enabling the results to be stored or a new program or training plan for example to be loaded.

Figure 3:
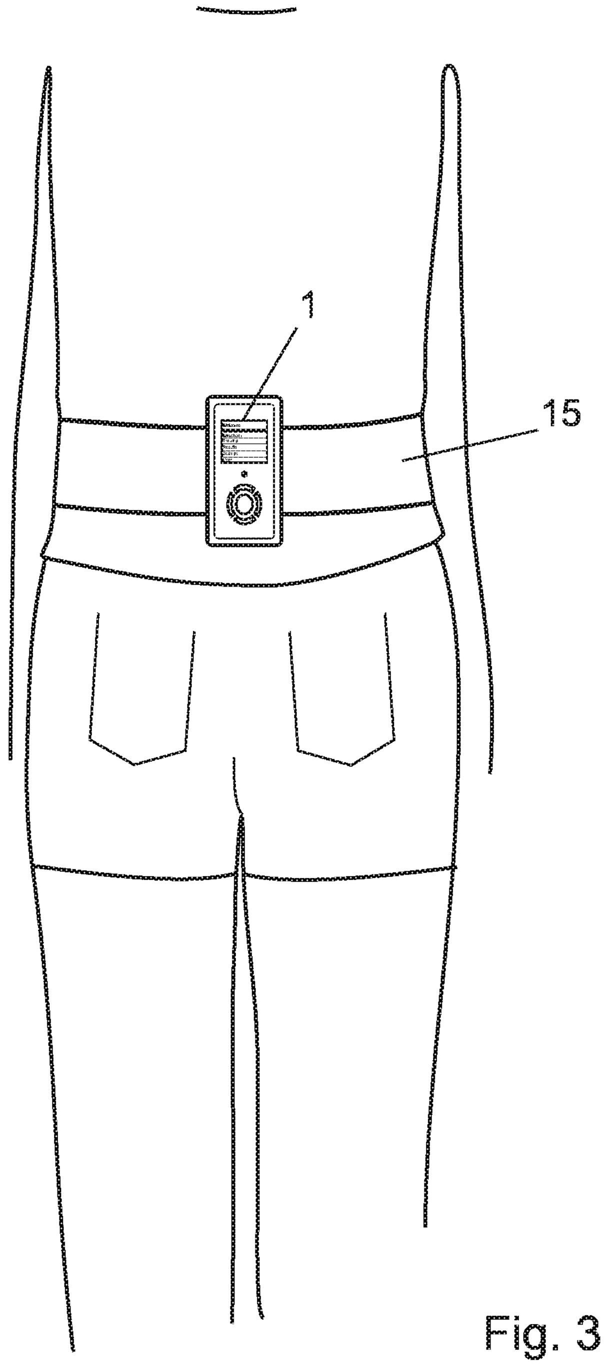
FIG. 3 illustrates diagrammatically the positioning of the device on the runner's torso by means of a belt (on the lower back or on the belly in order to be as close as possible to the center of gravity).

FIG. 3 illustrates diagrammatically the positioning of the device 1 in the lower back (hollow of the back) of a user 2 by means of a belt 15. This positioning also ensures a position very close to the runner's center of mass during practically the entire stride, without the device being able to vibrate or move relative to the center of mass. The device can also be placed in an equally advantageous position on the belly. Tests have shown that a positioning of the device on the members (for example on the wrist, on the foot or close to the knee) in now way allows this kind of measurement and analysis to be performed and thus excludes all the applications and inventions of the prior art that describe devices placed elsewhere than close to the athlete's center of gravity.

At the end and/or during a run, the device measures or determines by signal processing the following four basis parameters:

Acc (sequence of acceleration data)

$T_c$ (contact time)

$T_v$ (flight time)

T (duration of the run).

Furthermore, the user preferably enters the following parameters before or after the run:

D (distance of the run)

H (height in centimeters of the user)

M (user's mass).

The acceleration Acc is preferably obtained along several distinct axes.

In comparison to other prior art devices, the device thus supplies several distinct acceleration sequences, analyzed and stored independently from one another. In a preferred embodiment, the device determines a sequence of acceleration data in the vertical direction. In a preferred embodiment, the device further determines the acceleration in the anteroposterior direction in which the runner advances. In a preferred embodiment, the device can also supply a third sequence of acceleration data in the lateral direction, in order for example to determine the lateral sway movement of the athlete's body. These three directions can correspond to axes possibly different from the axes of the accelerometer.

Figure 4:
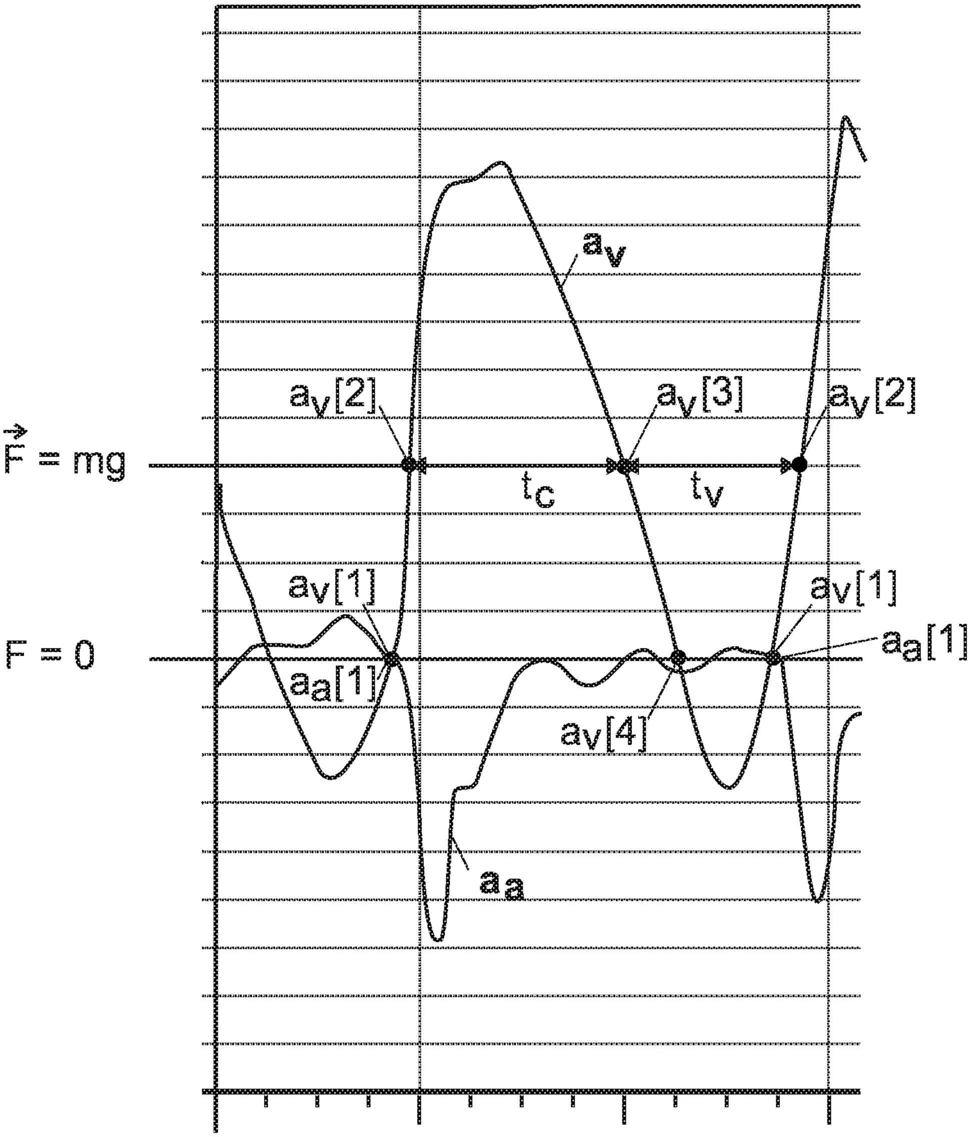
FIG. 4 illustrates an example of measurement of the acceleration in the vertical and anteroposterior direction during one stride.

FIG. 4 illustrates two curves showing the acceleration values $a_v$ according to the vertical direction and $a_a$ in the anteroposterior direction during one stride. The anteroposterior direction corresponds to the horizontal direction in which the runner progresses, i.e. a horizontal direction perpendicular to the rachis. The orientation of the device and/or of the accelerometer relative to the runner is measured at standstill and thus allows the "device-runner" frame of reference to be calibrated and transformed. The anteroposterior direction can initially be approximated and subsequently corrected after a rectilinear section of the run by measuring the direction in which the runner runs the longest distance. Advantageously, the frame of reference in which the sequences of acceleration data are measured is linked to the runner, and thus turns when the runner turns around a stadium for example. A correction of the frame of reference is preferably performed after calibration and/or during the run if the axes of the device's accelerometer do not coincide with the vertical and anteroposterior axes, for example in case of incorrect or inaccurate positioning of the device.

At the instant $a_v[1]$, the runner places the heel on the ground. The upwards vertical acceleration exerted by the ground on the foot increases rapidly whilst the anteroposterior acceleration $a_a$ becomes negative—the runner is slowed down by the shock of the heel on the ground.

The vertical acceleration then increases rapidly until the foot rests completely on the ground at the instant $a_v[2]$. At this moment, the center of gravity pivots forwards around the resting leg.

Between the instant $a_v[3]$ and the instant $a_v[4]$, the runner's foot starts to take off again; the vertical acceleration diminishes rapidly at this instant, whilst the anteroposterior acceleration is close to its maximum and the runner is propelled forwards.

From the instant $a_v[4]$ and until the next instant $a_v[1]$, the runner is in the air; the vertical acceleration is then negative and corresponds to gravity. The runner's center of gravity describes a ballistic trajectory with a roughly constant horizontal speed and a roughly parabolic trajectory.

The contact time during the stride thus corresponds to the interval $t_c$ between the instants $a_v[2]$ where the foot is contact with the ground and $a_v[3]$ where the same foot takes off again. The flight time $t_v$ corresponds to the complementary period between $a_v[3]$ and $a_v[2]$. These two durations can thus be determined directly from the sequences of acceleration data $a_v$ and possibly $a_a$, by simply signal processing and determination of particular points during the stride. In a preferred embodiment, the flight time and the contact time are calculated by averaging the flight times and contact times during all the strides made during a test; the less representative strides, e.g. at the beginning of the test, at the end of the test, when the value moves too far away from the average, or when the anteroposterior or lateral acceleration takes on unusual values, are preferably discarded from the average calculation.

The measurement of the biomechanical parameters of the stride during a run is advantageously performed during and immediately after a running test on a calibrated running course, for example in a stadium, on a road, in a sports hall, or by using a GPS-type satellite receiver in order to overcome the inaccuracies linked to measuring the travelled distance with an accelerometer and the shocks that might disrupt the accelerometer during a run on rugged terrain.

The duration of the exercise is preferably determined by means of the integrated chronograph. In one embodiment, the device invites the runner to run at a predetermined speed, either qualitatively ("run slowly", "run 400 m at your own pace" etc.), or quantitatively by emitting for example an acoustic signal inviting the user to slow down or, on the contrary, to speed up.

The beginning of the exercise is for example indicated by the device that can display or reproduce a countdown, by the user pressing a button, or detected by the accelerometer as soon as the user starts running after the program has started. Similarly, the end of the exercise can be indicated by the user, or detected by the accelerometer as soon as the user has travelled the expected distance or has sufficiently decelerated.

The user preferably enters the travelled distance into the device. For example, the device can display a message inviting the user to travel a predetermined distance, for example 100 meters, 400 meters, 1,000 meters or more, on a track; the biomechanical parameters of the stride are then displayed at the end of this exercise. The user can also enter him/herself the total distance travelled or select it in a menu. In another embodiment, it is possible to analyze in time the successive sequences and extract therefrom the variations of the different parameters described further above.

In one embodiment, the travelled distance is determined by a satellite receiver, for example a GPS receiver, integrated or connected to the device. It is possibly conceivable, though less accurate, to determine this distance using a double integration of the acceleration in the anteroposterior direction.

The other data that are preferably entered manually by the user include his/her mass in kilos and size in centimeters. Plausibility tests can be performed during the test, on the basis of the accelerometer's measurement results; for example, the length of the stride must be in a plausible ratio to the user's size.

At the end of (or during) the exercise, the device calculates a certain number of new biomechanical parameters relating to the runner's stride, on the basis of the above parameters measured by the device and/or entered by the user.

The average speed $V_{moy}$ over the distance D travelled in a running time T is calculated and displayed on the basis of the equation $$V_{moy} = D/T$$

Tests have shown that the use of the average speed $V_{moy}$ computed on the basis of the distance and total time surprisingly proves more accurate and more reliable than using the instantaneous speed V during each stride, which could be obtained by integration of the anteroposterior acceleration. It is however conceivable, in one embodiment, to use this measured instantaneous speed. In order to simplify the notation, the following formulae use the instantaneous speed V; it is however necessary to understand that it is preferable in most equations to use the average speed $V_{moy}$ calculated on the basis of the distance and travel time, or possibly the speed supplied by a possible GPS.

The number N of strides per minute during the period under consideration is the reverse of the average duration of a stride $T_v+T_c$ during this period:

$$N = 1/(T_v + T_c)$$

The average length of the stride $L_f$ can be calculated on the basis of the average speed over the running distance. The stride length is then equal to $$L_f = V*(T_c + T_v).$$

Figure 6:
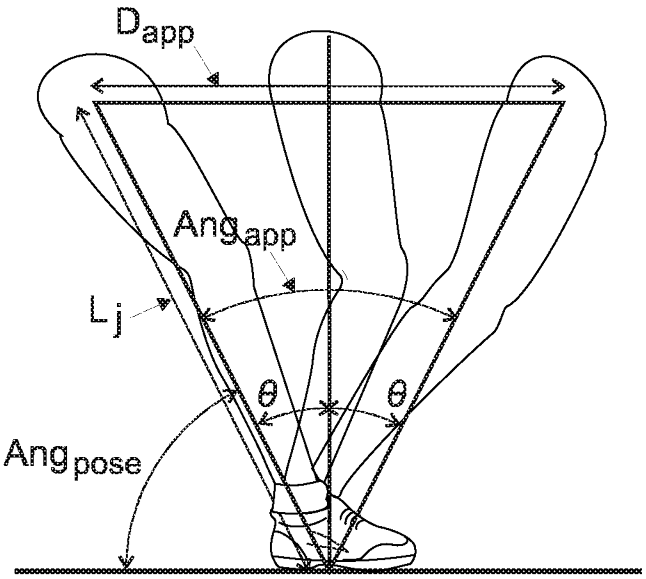
FIG. 6 illustrates diagrammatically the landing angle of the leg, the angle of the leg's area of contact with the ground and the distance during contact.

Another useful parameter for evaluating the stride efficiency is constituted by the distance $D_{appui}$ travelled by the center of gravity CG whilst the foot is resting on the ground. It has been observed that this parameter can also be obtained from the acceleration data, for example through the equation $$D_{appui} = V*T_c$$

or by using the instantaneous speed during each stride or each contact on the ground. FIG. 6 illustrates diagrammatically and approximately the distance $D_{appui}$.

The speed $V_{deco}$ along the vertical component during the foot's takeoff depends on the average acceleration $A_{moy}$ and on the contact time $T_c$:

$$V_{deco} = A_{moy}*T_c/2$$

Figure 5:
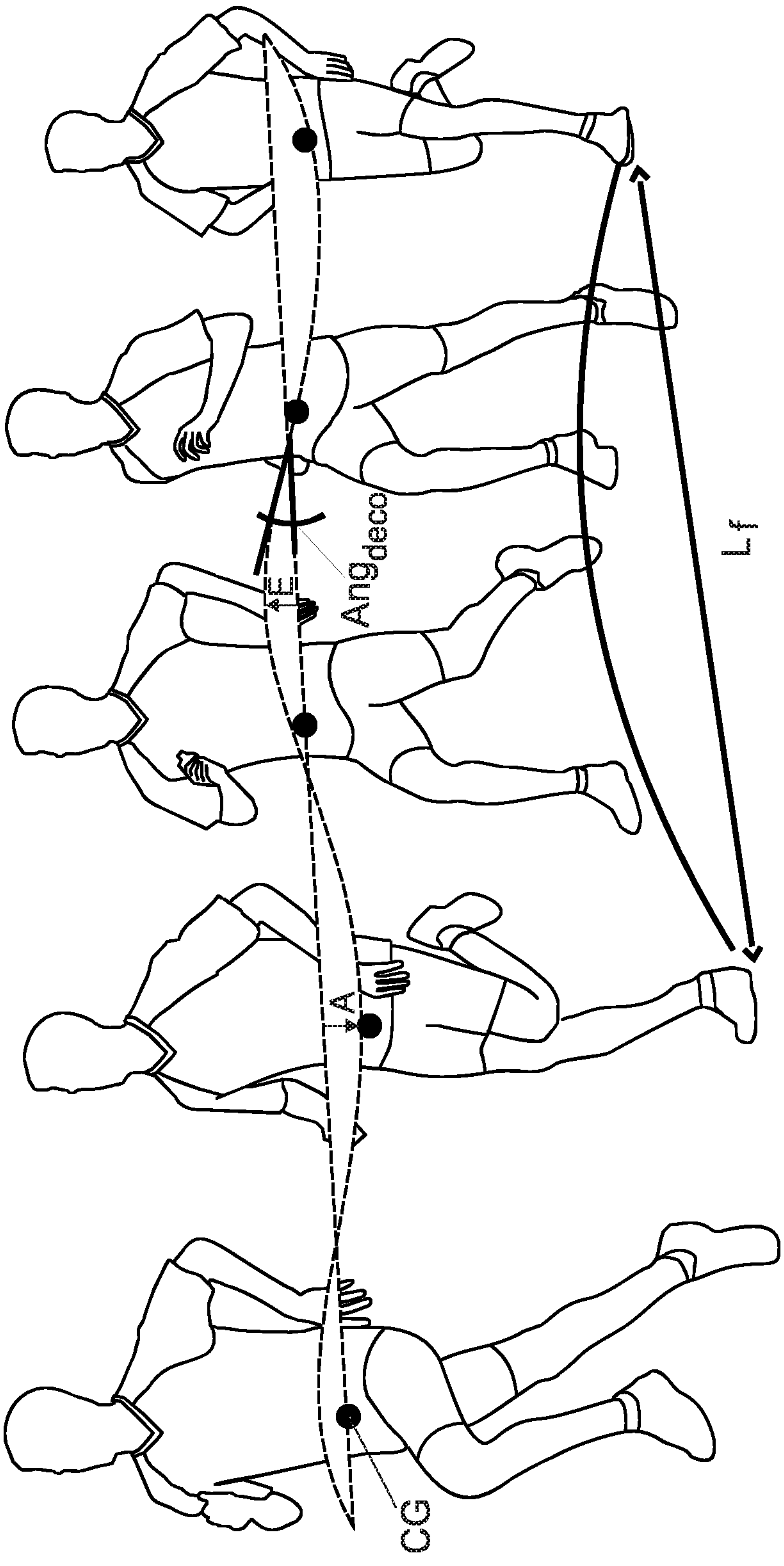
FIG. 5 illustrates diagrammatically the oscillations of the runner's center of mass during one stride (undulation, elevation, lowering, takeoff angle of the center of gravity).

It has also been observed that the takeoff angle of the center of gravity $Ang_{deco}$ illustrated in FIG. 5 supplies very useful information for assessing and improving the stride. It has furthermore been observed for the first time that a camera is not indispensable for measuring this angle, which can be evaluated reliably from the acceleration sequences supplied by an accelerometer such as described, in particular acceleration sequences in the vertical direction. The takeoff angle indicates the angle formed by the trajectory of the center of gravity and the anteroposterior direction. This takeoff angle can be obtained from the average speed $V_{moy}$ and the vertical speed $V_{deco}$ at the moment of takeoff thanks to the equation $$Ang_{deco} = 180/\pi*\tan-1(V_{moy}/V_{deco})$$

In the same way, it is possible to determine, without camera and from the acceleration data, the angle of the resting area $Ang_{app}$ (illustrated in FIG. 6 and corresponding to the angle travelled by the leg with a length $L_j$ when the foot is resting on the ground) with the formula:

$$Ang_{app} = 180/\pi*(V_{moy}*T_c/L_j)$$

The leg's landing angle at the moment when the foot touches the ground is also illustrated in FIG. 6. It can be estimated, still on the basis of the data from the accelerometer and for the first time without using a camera, by means of the equation:

$$Ang_{pose} = (180 - Ang_{app})/2$$

The maximum force $F_{max}$ exerted by the ground on the foot of a runner with a mass M can be determined by means of the equation:

$$F_{max} = M*g*\pi/2*(T_v/T_c + 1)$$

The average force when resting, normalized relative to the body weight $F_{moy}$, is itself equal to:

$$F_{moy} = A_{moy}/g + 1$$

The lowering A of the center of mass at each stride can be obtained as a function of the maximum bearing force $F_{max}$, of the contact time $T_c$ and of the runner's mass M with the aid of the formula $$A = f(F_{max}, T_c, M) = |-(F_{max}*T_c^2)/(M*\pi^2) + (G*T_c^2)/8|$$

In the same way, the elevation E of the center of mass can be calculated with the formula $$E = V_{deco}^2/(2*G)$$

wherein $V_{deco}$ corresponds to the vertical speed at takeoff.

FIG. 5 illustrates diagrammatically the signification of the parameters A and E during one stride. An efficient running style generally involves a reduced lowering and elevation of the center of gravity CG that moves ideally in a horizontal plane. It is possible to calculate an undulation parameter of the center of gravity:

$$\text{undulation} = \text{lowering} + \text{elevation}$$

resulting from the sum of these two parameters.

Many runners are also interested in muscular stiffness, which yields information on the leg muscles' ability to resist deformation during each impact on the ground or whether they no longer produce a sufficient tension necessary to avoid too great a lowering of the center of gravity which impairs performance. A stiffness parameter can be calculated depending on the maximum force $F_{max}$ exerted by the ground on the foot and on the lowering A, whose value generally corresponds to the instant when this maximum force is exerted:

$$\text{stiffness} = F_{max}/A$$

Many runners are also interested in the regularity of their stride; it is more efficient to run in a regular fashion than in an irregular manner. The prior art devices, however, do not allow the stride regularity to be easily measured. It has however been observed that the sequences of acceleration data can be used for calculating a reliable and representative regularity index, for example on the basis of the speed dispersion, stride length dispersion, flight time dispersion etc. Tests have however shown that it is particularly interesting to determine a regularity index as a function of the reactivity $T_v/T_c$, for example by calculating the reactivity dispersion.

Irregular running is often evidence of fatigue; the flight time tends to diminish and the contact time with the ground to increase when the runner gets tired. It is thus possible to calculate a level of fatigue on the basis of the regularity, for example with the aid of the formula:

$$\text{Fatigue} = 1 - \frac{\sum_{i=1}^{n} Re\,gularit\acute{e}(i)}{n \cdot Re\,gularit\acute{e}(1)}$$

It is also possible to determine and take an interest for example in the vertical mechanical work (depending on the lowering or undulation of the center of gravity) and/or on the horizontal mechanical work.

The efficiency of the stride can also be affected by an asymmetry between each of the legs. A level of asymmetry can for example be calculated by comparing or performing a differential between at least one parameter of each of the legs measured with the accelerometer. During particularly significant tests, it has proved possible to determine the difference between the contact time of each of the legs, according to the equation:

$$\text{asymmetry} = (T_c\text{max} - T_c\text{min})/T_c\text{min}$$

It would also be possible to determine for example the difference between the flight time of each of the legs.

An asymmetry is sometimes also a warning sign of a risk of injury or poorly healed injury. It is thus possible to calculate a risk of injury as a function of the asymmetry, for example by means of the equation:

$$\text{Risk of injury} = f(\text{asymmetry}) = \text{R\_injury} = 1 - \frac{\sum_{i=1}^{n} Asy(i)}{n \cdot Asy_{max}}$$

The set of different parameters above cannot be determined with the prior art devices; each individual parameter has its own meaning, useful for the athlete and coach, and can be determined independently of the other parameters.

It is possible to measure these parameters over an entire test, for example by calculating the average value of each parameter during a test over 400 meters or over another length. It is also possible to calculate a sequence of instantaneous values in order to observe the evolution of each parameter during the test, for example the length of each stride, etc. In another embodiment, the travelled distance is automatically or manually segmented into different sections and the parameters corresponding to each section are calculated and displayed. The sections can for example correspond to predetermined distances, for example by breaking up a distance or even by parameterizing measurements of several seconds at regular intervals or at a precise location of the running course by deliberately pressing on the device's button. The device allows the selection of the parameters and of the section that are to be displayed.

In a variant embodiment, the sections correspond to segments with different characteristics, for example segments with a different slope or segments travelled at different speeds. Parameters can also be calculated on the basis of averages calculated during discontinuous and automatically regrouped segments, for example in order to calculate averages of parameters over all the uphill or downhill segments. The segmentation can also be performed automatically on the basis of data from a GPS-type satellite receiver for example.

A measurement of biomechanical parameters can be performed as indicated during a test on a calibrated distance, for example around a lap of a sports field track. It is also possible additionally to perform a measurement and display during normal training sessions, for example whilst jogging outdoors, during a competition etc. Although the measurements are disturbed by shocks on the terrain and by the inaccuracy as to the travelled distance, this mode of operation makes it possible to measure the same parameters in other conditions or other parameters such as for example the evolution of the stride during a long-lasting training session or when the athlete moves on uneven or non level ground. It is for example possible to supply differentiated results for a run on the flat or uphill or downhill. This inclination can be determined by a satellite receiver, by the user him/herself or by interpreting the signals produced by the accelerometer in the vertical and/or another direction.

The device displays and/or reproduces biomechanical parameters related to the stride immediately after the exercise or even during the exercise. The runner can thus become aware during respectively after the run of the evolution of the parameters. For example, the user can be notified when s/he is reducing the stride length or the horizontal displacement of the center of mass at each stride, or when his/her muscle stiffness diminishes, which can be a warning or indicative sign of muscular fatigue.

Tests have shown that the device makes is possible to measure and evaluate the above parameters with significant accuracy and low dispersion values, by using the above formulae. It is thus possible to determine specific training programs aiming to improve both the technical qualities and the physical abilities of the runner whilst preventing injuries and risks of fatigue and improving the stride efficiency.

The device advantageously allows muscle-training schedules to be generated on the basis of the measured parameters and which will improve the running style and stride efficiency. For example, the device can propose gymnastic, muscle strengthening or stretching exercises in order to reinforce certain parameters, in a manner customized to each runner. The exercises and schedules proposed for training can also include personalized running sessions, at a rhythm and/or with indications supplied visually and/or acoustically by the device.

The invention claimed is:

1. A method for preventing injuries to a runner during a running activity, the method comprising:

fastening a portable device proximate to a center of gravity of the runner, the portable device including a triaxial accelerometer, a digital processor, and a display;

measuring, with the triaxial accelerometer, a sequence of acceleration data including vertical acceleration data and lateral acceleration data while the runner performs the running activity over a particular distance along a running course during a time period;

processing, with the digital processor, the vertical acceleration data separately from the lateral acceleration data;

determining, during or at an end of the running activity, an asymmetry of movement of the runner based on motion of the center of gravity of the runner, the acceleration data, the particular distance, and the time period;

calculating a regularity index of the running activity based on the asymmetry of movement;

calculating a regularity index of the running activity based on the acceleration data classifying the runner as one of a plurality of runner types based on the asymmetry of movement, the regularity index, and the fatigue level indicator;

selecting, by the digital processor, a shoe class or pair of shoes for the runner based on the classifying; and displaying, on the display of the portable device, the asymmetry of movement and the selected shoe class or pair of shoes.

2. The method of claim 1, wherein the displaying further comprises:

displaying at least one of: a training plan, a radar chart, or a Kiviat diagram.

3. The method of claim 1, wherein selecting the shoe class or pair of shoes comprises selecting a sport equipment article for the runner based on the asymmetry of movement of the runner.

4. The method of claim 3, wherein the sport equipment article is the pair of shoes.

5. The method of claim 3, wherein the sport equipment article improves an efficiency of displacement of the runner and/or a protection of a musculotendinous system of the runner.

6. The method of claim 1, further comprising:

defining a first class of shoes adapted for a first type of runner and a second class of shoes adapted for a second type of runner;

wherein classifying the runner comprises classifying the runner as the first type of runner or the second type of runner based on the asymmetry of movement of the runner; and wherein selecting the shoe class or pair of shoes comprises selecting the shoe class or pair of shoes based on the asymmetry of movement of the runner and the classifying.

7. The method of claim 1, further comprising:

defining a first class of shoes adapted for a pronating runner, a second class of shoes adapted for a supinating runner, and a third class of shoes adapted for a neutral runner;

wherein classifying the runner comprises classifying the runner as the pronating runner, the supinating runner, or the neutral runner based on the asymmetry of movement of the runner; and wherein selecting the shoe class or pair of shoes comprises selecting the shoe class or pair of shoes based on the asymmetry of movement of the runner and the classifying.

8. The method of claim 1, wherein the sequence of acceleration data is further measured along an anteroposterior direction using the triaxial accelerometer.

9. The method of claim 8, wherein the lateral acceleration data is processed separately from the vertical acceleration data and the anteroposterior acceleration data.

10. The method of claim 1, wherein the determined asymmetry of movement of the runner is based on asymmetry between at least one movement of a left leg and at least one corresponding movement of a right leg.

11. The method of claim 1, further comprising:

determining an injury risk indicator calculated based on the asymmetry of movement of the runner.

12. The method of claim 1, further comprising:

calculating at least one of a balance, explosive power, mobility, resistance, or stability of the runner based on the asymmetry of movement of the runner.

13. The method of claim 1, wherein the device is portable device is configured to execute a computer program for performing the method.

14. The method of claim 13, wherein the portable device is a mobile phone.

15. The method of claim 1, wherein the portable device is fastened to a torso of the runner.

16. The method of claim 1, wherein selecting the shoe class or pair of shoes is based on the asymmetry of movement of the runner and the regularity index.

17. The method of claim 16, wherein selecting the shoe class or pair of shoes is further based on the fatigue level indicator.

18. The method of claim 1, wherein the determined asymmetry of movement of the runner is based on asymmetry between at least one forward movement of the runner and at least one corresponding backward movement of the runner.

19. A non-transitory computer readable medium storing instructions for preventing injuries to a runner during a running activity, the instructions, when executed by a digital processor of a portable device including a triaxial accelerometer and a display, cause the portable device to execute a method comprising:

measuring, with the triaxial accelerometer, a sequence of acceleration data including vertical acceleration data and lateral acceleration data while the portable device is fastened proximate to a center of gravity of the runner and the runner performs the running activity over a particular distance along a running course during a time period;

processing, with the digital processor, the vertical acceleration data separately from the lateral acceleration data;

determining, during or at an end of the running activity, an asymmetry of movement of the runner based on motion of the center of gravity of the runner, the acceleration data, the particular distance, and the time period;

calculating a regularity index of the running activity based on the asymmetry of movement;

calculating a regularity index of the running activity based on the acceleration data;

classifying the runner as one of a plurality of runner types based on the asymmetry of movement, the regularity index, and the fatigue level indicator;

selecting, by the digital processor, a shoe class or pair of shoes for the runner based on the classifying; and displaying, on the display of the portable device, the asymmetry of movement and the selected shoe class or pair of shoes.

20. A wearable device configured for preventing injuries to a runner during a running activity, the wearable device comprising:

a fastening system configured to mechanically couple the wearable device proximate to a center of gravity of the runner;

a triaxial accelerometer;

a display; and a digital processor communicatively coupled to the triaxial accelerometer and the display, wherein the digital processor is configured to:

measure, using the triaxial accelerometer, a sequence of acceleration data including vertical acceleration data and lateral acceleration data while the runner performs the running activity over a distance along a running course during a time period;

process the vertical acceleration data separately from the lateral acceleration data;

determine, during or at an end of the running activity, an asymmetry of movement of the runner based on motion of the center of gravity of the runner, the acceleration data, the distance, and the time period;

calculate a regularity index of the running activity based on the asymmetry of movement;

calculate a regularity index of the running activity based on the acceleration data;

classify the runner as one of a plurality of runner types based on the asymmetry of movement, the regularity index, and the fatigue level indicator;

select a shoe class or pair of shoes for the runner based on the classification; and display, on the display, the asymmetry of movement and the selected shoe class or pair of shoes.

* * * * *